United States Patent
Ono et al.

[11] Patent Number: 5,827,529
[45] Date of Patent: Oct. 27, 1998

[54] EXTERNAL PREPARATION FOR APPLICATION TO THE SKIN CONTAINING LIDOCAINE

[75] Inventors: Masahiro Ono; Mitsuji Akazawa; Michiko Seki; Kiyomi Iwamoto; Ryoji Konishi, all of Kagawa-ken, Japan

[73] Assignee: Teikoku Seiyaku Kabushiki Kaisha, Kagawa-Ken, Japan

[21] Appl. No.: 258,378

[22] Filed: Jun. 10, 1994

Related U.S. Application Data

[63] Continuation of Ser. No. 860,008, Mar. 30, 1992, abandoned.

[30] Foreign Application Priority Data

Mar. 30, 1991 [JP] Japan ................................ 3-067353

[51] Int. Cl.⁶ ..................... A61K 9/00; A61K 9/70
[52] U.S. Cl. .................. 424/448; 424/985; 424/486; 424/487; 424/489; 424/78.02; 514/817; 514/944
[58] Field of Search ................ 424/401, 78.02, 424/448, 485–489, 449; 514/817, 944

[56] References Cited

U.S. PATENT DOCUMENTS

| | | | |
|---|---|---|---|
| 3,797,494 | 3/1974 | Zaffaroni | 424/448 |
| 4,628,063 | 12/1986 | Haines et al. | |
| 4,834,978 | 5/1989 | Nuwayser | 424/448 |
| 4,914,131 | 4/1990 | Haines et al. | |
| 5,002,974 | 3/1991 | Genia | 514/782 |
| 5,059,189 | 10/1991 | Cliento | 424/449 |
| 5,066,494 | 11/1991 | Becher | 424/448 |
| 5,120,544 | 6/1992 | Henley | 424/443 |

FOREIGN PATENT DOCUMENTS

| | | |
|---|---|---|
| 0388306 | 9/1990 | European Pat. Off. |
| WO8910740 | 11/1989 | WIPO |

OTHER PUBLICATIONS

Database: WPIL, accession No. 82–86701E [41], Derwent Publications Ltd., London, GB. (no date).
Database: WPIL, accession No. 87–010530 [02], Derwent Publications Ltd., London, GB. (no date).

*Primary Examiner*—Sally Gardner-Lane
*Attorney, Agent, or Firm*—Birch, Stewart, Kolasch, & Birch, LLP

[57] ABSTRACT

An external preparation for application to the skin containing lidocaine which comprises a drug-retaining layer placed on a support, wherein said drug-retaining layer comprises an adhesive gel base and 1 to 10% by weight of lidocaine, said base comprising a water-soluble high molecular weight substance, water and a water-retaining agent, which can release the active lidocaine gradually and constantly so that lidocaine is transdermally absorbed for a long period of time.

6 Claims, 2 Drawing Sheets

EXTERNAL PREPARATION FOR APPLICATION TO THE SKIN CONTAINING LIDOCAINE

This application is a continuation of application Ser. No. 07/860,008, filed on Mar. 30, 1992, now abandoned.

The present invention relates to an external preparation for application to the skin containing lidocaine, more particularly, to an external preparation for application to the skin wherein lidocaine or a salt thereof as an active ingredient is dispersed or dissolved in a water-soluble high molecular weight substance in an adhesive gel base which is spread onto a support, and said active ingredient can be gradually and constantly released from the preparation stably so that it can be transdermally absorbed for a long period of time.

PRIOR ART

In recent years, there have been conducted nerve block therapy, acupuncture, iontophoresis therapy, or administration of central analgesics or antidepressants in order to cure herpes zoster neuralgia and postherpetic neuralgia which occur in the aged at a relatively high frequency.

Typical drug used in nerve block therapy is lidocaine. Lidocaine, which has been developed as local anesthetics, has surface, infiltration and conduction anesthetic actions and has been mainly used as surface anesthetics in the field of dentistry. Lidocaine is widely used as a primary drug for treatment of extrasystole, acute myocardial infarction, and ventricular arrhythmia occurred in surgical operation of heart.

In order to use lidocaine for treatment of herpes zoster neuralgia and postherpetic neuralgia, it is administered into the epidural cavity via a block needle in case of nerve block therapy. However, this method has the following disadvantages.

(i) Although the drug is quickly conveyed to the tissue to be treated, the treatment should be conducted with monitoring the blood pressure, heart rate and systemic conditions.

(ii) There is a high possibility of inducing systemic side effects in the aged or patients with heart disease or liver disease.

(iii) Since the treatment cannot be conducted at home, patients must go to hospital at every treatment or must be hospitalized.

(iv) Each treatment requires a long period of time.

Another means of treatment for transdermal absorption is the use of ointments. Although the ointment can advantageously be applied to such portions as head, face, etc. to which the external preparations for application to the skin is hardly applied, it has still disadvantages as follows:

(i) It is difficult to quantitatively administer the drug, and hand, finger, clothes etc. are stained quite often. In order to prevent this, the applied portions can be covered with gauze etc. but this is troublesome.

(ii) As the result of volatilization of the solvent in the preparation, the drug is crystallized out, and hence, the transdermal absorption of the drug is lowered. In order to prevent this, the applied portions can be covered with film etc. but the water content in horny layer is excessively increased, and hence, there can be predicted the occurrence of dermatological alergies such as eczema, hives, etc.

(iii) In the treatment of herpes zoster neuralgia and postherpetic neuralgia, the portion to be treated is preferably continuously provided with the drug. Since lidocaine is quickly metabolized, the ointment should be applied for several times a day.

As to iontophoresis therapy which recently draws public attention, this method still has the following disadvantages in spite of many advantages as the local therapy without pain.

(i) Since a special equipment is necessary for the treatment, patient must go to hospital at every treatment. In addition, it takes time and trouble for the treatment.

(ii) A range of each treatment is limited and the conditions for applying electric current should be changed for each individual.

(iii) Since electric current is directly applied to the skin, there is a possibility of occurrence of secondary side effects such as burn though this is a rare case.

SUMMARY DESCRIPTION OF THE INVENTION

Under the circumstances, the present inventors have intensively studied in order to develop external preparations for application to the skin containing lidocaine suitable for transdermal administration, and as a result, have found that, by dispersing or dissolving lidocaine in a water-soluble high molecular weight substance, there can be obtained an external preparation for application to the skin for transdermal absorption of the drug, which shows an excellent adhesion, has excellent property of controlling the release of the drug and allows for transdermal absorption of the drug for a long period of time.

An object of the present invention is to provide an external preparation for application to the skin containing lidocaine which comprises a drug-retaining layer placed on a support, wherein said drug-retaining layer comprises an adhesive gel base and 1 to 10% (% by weight, hereinafter the same) of lidocaine, said base comprising a water-soluble high molecular weight substance, water and a water-retaining agent.

These and other objects and advantages of the present invention will be apparent to those skilled in the art from the following description.

DETAILED DESCRIPTION OF THE INVENTION

Figure 1:
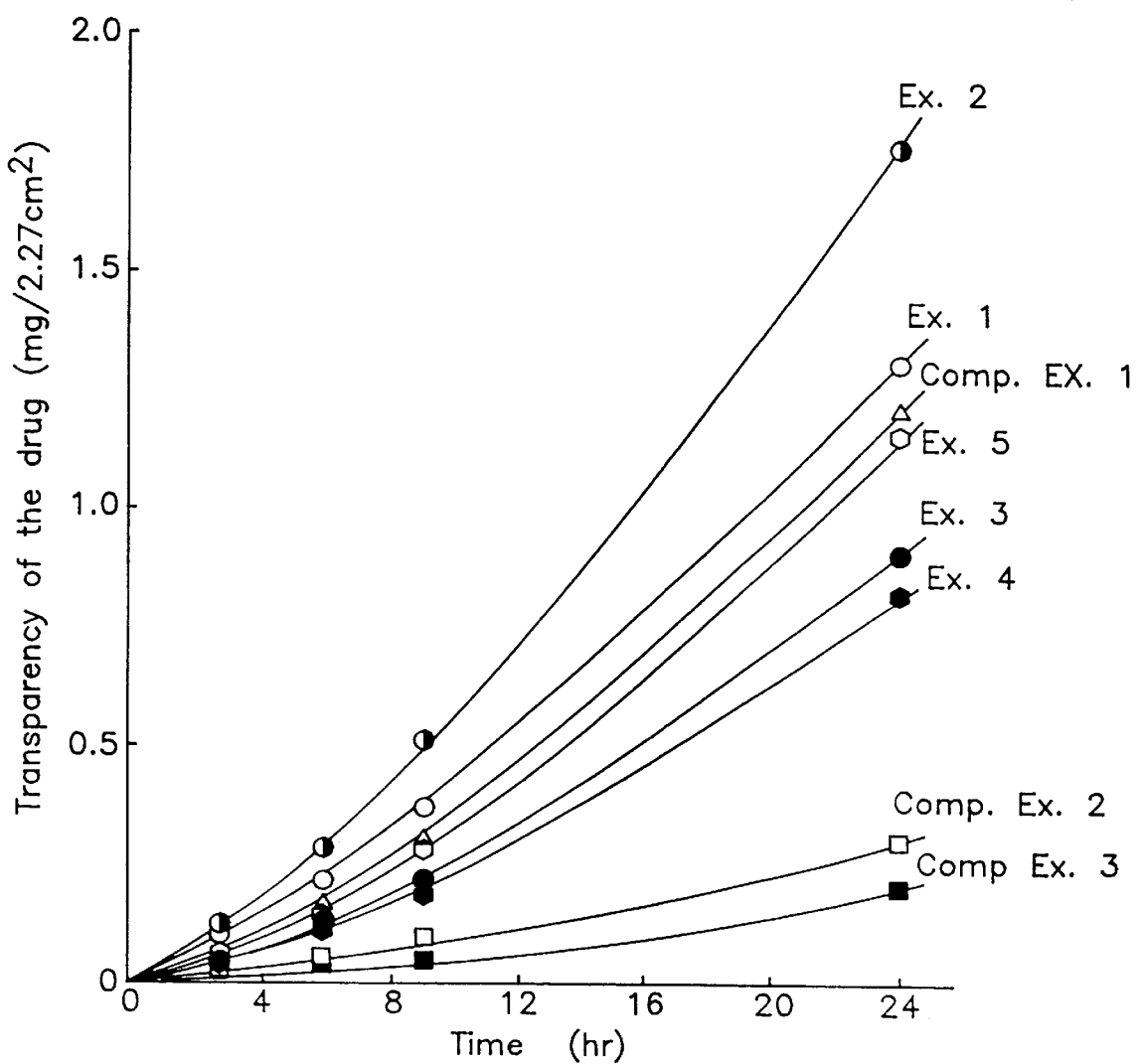
FIG. 1 is a graph showing a permeability of the drug with the passage of time in case of the preparations of Examples 1 to 5 in comparison with the ointment of Comparative Example 1 and the plasters of Comparative Examples 2 and 3.

The adhesive gel base used in the preparation of the present invention comprises a water-soluble high molecular weight substance, water and a water-retaining agent as essential components. The water-soluble high molecular weight substance includes gelatin, starch, agar, mannan, alginic acid, polyacrylic acid, a salt of polyacrylic acid, dextrin, methylcellulose, methylcellulose sodium, carboxymethylcellulose, carboxymethylcellulose sodium, polyvinyl alcohol, polyvinyl pyrrolidone, a copolymer of methyl vinyl ether and maleic anhydride, gum arabic, tragacanth, karaya gum, locust bean gum, etc. There can also be used a metallic salt of the above substances and cross-linked products of the above substances with an organic or inorganic cross-linking agent. One or more kinds of the water-soluble high molecular weight substance are used in the adhesive gel base. An amount of the water-soluble high molecular weight substance is in a range of 0.5 to 50% (% by weight, hereinafter the same), preferably 5 to 25%.

Water contained in the adhesive gel base increases the swelling of the skin horny layer and the permeability of the drug. The water context is preferably in a range of 10 to 70%, more preferably 20 to 50%.

The water-retaining agent used in the preparation of the invention prevents the volatilization of water contained in the adhesive gel base so that the water content in the adhesive gel base is maintained at a constant level during storage and using of the preparation because the volatilization of water affects on the release rate of the drug to the skin. The water-retaining agent includes, for example, glycols or saccharides such as ethylene glycol, diethylene glycol, polyethylene glycol, glycerin, sorbitol, martitol, propylene glycol, 1,3-butylene glycol, etc. One or more kinds of the water-retaining agent are used. An amount of the water-retaining agent in the adhesive gel base is preferably in a range of 1 to 70%, more preferably 10 to 60%.

In order to retain the water content in the adhesive gel base more sufficiently, an extremely highly water-absorbable high molecular weight substance may also be used. Such an extremely highly water-absorbable high molecular weight substance includes, for example, a graft copolymer of starch and acrylonitrile, a graft copolymer of starch and acrylic acid, a graft copolymer of starch and styrenesulfonic acid, a graft copolymer of starch and vinyl-sulfonic acid, a cross-linked product of polyvinyl alcohol, a saponification product of acrylic acid/vinyl acetate copolymer, a cross-linked product of polyethylene glycol diacrylate, etc. An amount of the extremely highly water-absorbable high molecular weight substance in the adhesive gel base is preferably in a range of 0 to 20%, more preferable 0.01 to 10%.

If necessary, there can also be used a conventional absorbing agent such as salicylic acid, hyaluronic acid, oleic acids N,N-diethyl-m-toluamide, n-butyl stearate, benzyl alcohol, isopropyl myristate, isopropyl palmitate, polypropylene glycol, crotamiton, diethyl sebacate, N-methylpyrrolidone, N-ethylpyrrolidone, lauryl alcohol, etc., and a surfactant for emulsifying the absorbing agent in the gel base, including, for example, polyoxyethylene sorbitan monooleate, polyoxyethylene sorbitan monostearate, sorbitan monooleate, sorbitan monopalmitate, etc. In addition, a preserving agent, an antioxidant, etc. may also be used in a suitable amount. Any kind and amount of antioxidant or preserving agent may be used unless they affect on the control release of the drug and the stimuli to the skin.

The adhesive gel base comprising the above components preferably has a pH value of 5 to 9 in view of the stimuli to the skin and the stability of the drug. The pH may be adjusted to the above range by adding an alkaline substance such as sodium hydroxide or an amine such as triethanolamine, diisopropanolamine, etc. or an acid substance such as tartaric acid, citric acid, malic acid, lactic acid, acetic acid, phthalic acid, etc.

The external preparation for application to the skin containing lidocaine of the invention can be prepared by adding the drug, i.e. lidocaine or a salt thereof such as lidocaine hydrochloride, in an effective amount to the above-mentioned adhesive gel base to prepare a drug-retaining layer, the content of the drug being in a range of 0.5 to 15.0%, preferably 2.5 to 10.0%, and spreading the drug-retaining layer onto a suitable support. The thus prepared drug-retaining layer is spread onto the support in an amount of 500 to 2000 g/m$^2$.

In order to protect the drug-retaining layer from the volatilization of water therein, a liner made of a suitable material may also be adhered to the surface of said layer. The support is preferably made of a flexible material which is capable of fitting in the movement of human body and includes, for example, various non-woven fabrics, woven fabrics, spandex, flannel, or a laminate of these materials with polyethylene film, polyethylene glycol terephthalate film, polyvinyl chloride film, ethylene-vinyl acetate copolymer film, polyurethane film, and the like.

The external preparation for application to the skin of the invention is capable of releasing the drug quantitatively, is easily handled, and is capable of being applied for a long period of time. In addition, the external preparation of the invention has the following advantages:

(i) Since the preparation of the invention is externally applied to the skin, the first-pass effect in liver (that is, decomposition of lidocaine occurred when administered orally) can be avoided, and hence, the bioavailability can be increased.

(ii) Since the preparation of the invention is externally applied to the skin, the drug is continuously released for a long period of time, and hence, it is expected that the activity of the drug is stably exhibited. In addition, the preparation of the invention can be administered less frequently, and hence, the compliance of patients can be improved.

(iii) The patients suffering from postherpetic neuralgia sometimes feel pain even by the touch of wind or rubbing with cloths. In such a case, the pain can be reduced by covering the surface of the skin by the external preparation of the invention.

(iv) The preparation of the invention can be administered regardless of patient's age, health conditions, conditions of digestive organs such as stomach or intestines or function of liver, or food.

The present invention is explained in more detail by the following Examples, Comparative Examples and Experiments but should not be construed to be limited thereto. In the following Examples and Comparative Examples, "part" or "parts" means "part by weight" or "parts by weight" unless otherwise..mentioned.

EXAMPLE 1

| | |
|---|---|
| Lidocaine | 5 parts |
| D-Sorbitol | 15 parts |
| Glycerin | 20 parts |
| Propylene glycol | 10 parts |
| Sodium polyacrylate | 4 parts |
| Carboxymethylcellulose sodium | 5 parts |
| Polyacrylic acid | 2 parts |
| Methyl paraoxybenzoate | 0.1 part |
| Propyl paraoxybenzoate | 0.05 part |
| Aluminum hydroxide | 0.3 part |
| Purified water | q.s. |
| Total amount | 100 parts |

D-Sorbitol and polyacrylic acid are added to purified water and the mixture is stirred. To the mixture is further added a solution of lidocaine in propylene glycol and the mixture is stirred. Then, to the mixture is added a dispersion of sodium polyacrylate, carboxymethylcellulose sodium, aluminum hydroxide, methyl paraoxybenzoate and propyl paraoxybenzoate in glycerin and the mixture is sufficiently stirred until a uniform mixture is obtained. The obtained base is applied onto and spread over a non-woven fabric at 1000 g/m² and to the base is adhered a liner made of polyethylene terephthalate processed with silicone. The obtained preparation is cut into a desired size to give an external preparation for application to the skin which has a pH value of 7 and contains 5 mg/cm² of lidocaine.

EXAMPLE 2

| Lidocaine | 10 parts |
| --- | --- |
| D-Sorbitol | 10 parts |
| Glycerin | 20 parts |
| Propylene glycol | 10 parts |
| Sodium polyacrylate | 4 parts |
| Carboxymethylcellulose sodium | 5 parts |
| Polyacrylic acid | 3 parts |
| Methyl paraoxybenozate | 0.1 part |
| Propyl paraoxybenzoate | 0.05 part |
| Aluminum hydroxide | 0.3 part |
| Purified water | q.s. |
| Total amount | 100 parts |

The above components are mixed together in the same manner as in Example 1 to give a base. The obtained base is applied onto and spread over a non-woven fabric at 1000 g/m² and to the base is adhered a liner made of polyethylene terephthalate processed with silicone. The obtained preparation is cut into a desired size to give an external preparation for application to the skin which has a pH value of 7 and contains 10 mg/cm² of lidocaine.

EXAMPLE 3

| Lidocaine | 5 parts |
| --- | --- |
| Gelatin | 1 part |
| Kaolin | 1 part |
| D-Sorbitol | 15 parts |
| Glycerin | 20 parts |
| Propylene glycol | 10 parts |
| Sodium polyacrylate | 5 parts |
| Carboxymethylcellulose sodium | 5 parts |
| Polyacrylic acid | 2 parts |
| Urea | 1 part |
| Methyl paraoxybenzoate | 0.1 part |
| Propyl paraoxybenzoate | 0.05 part |
| Aluminum hydroxide | 0.3 part |
| Purified water | q.s. |
| Total amount | 100 parts |

To a solution of gelatin and polyacrylic acid in purified water are added kaolin, D-sorbitol and urea and the mixture is well stirred. To the mixture is further added a solution of lidocaine in propylene glycol and the mixture is stirred. To the mixture is then added a dispersion of sodium polyacrylate, carboxymethylcellulose sodium, aluminum hydroxide, methyl paraoxybenzoate and propyl paraoxybenzoate in glycerin and the mixture is stirred until a uniform mixture is obtained. The obtained base is applied onto and spread over a non-woven fabric at 1000 g/m² and to the base is adhered a liner made of polyethylene terephthalate processed with silicone. The obtained preparation is cut into a desired size to give an external preparation for application to the skin which has a pH value of 6 and contains 5 mg/cm² of lidocaine.

EXAMPLE 4

| Lidocaine | 5 parts |
| --- | --- |
| Gelatin | 1 part |
| Kaolin | 1 part |
| D-Sorbitol | 15 parts |
| Glycerin | 20 parts |
| Propylene glycol | 5 parts |
| Sodium polyacrylate | 5 parts |
| Carboxymethylcellulose sodium | 5 parts |
| Polyacrylic acid | 2 parts |
| Urea | 1 part |
| Tartaric acid | 1.5 parts |
| Methyl paraoxybenzoate | 0.1 part |
| Propyl paraoxybenzoate | 0.05 part |
| Dihydroxy aluminum aminoacetate | 0.3 part |
| Purified water | q.s. |
| Total amount | 100 parts |

The above components are mixed in the same manner as in Example 3 to give a base. The obtained base is applied onto and spread over a non-woven fabric at 1000 g/m² and to the base is adhered a liner made of polyethylene terephthalate processed with silicone. The obtained preparation is cut into a desired size to give an external preparation for application to the skin which has a pH value of 6 and contains 5 mg/cm² of lidocaine.

EXAMPLE 5

| Lidocaine | 5 parts |
| --- | --- |
| D-Sorbitol | 15 parts |
| Glycerin | 20 parts |
| Propylene glycol | 10 parts |
| Sodium polyacrylate | 4 parts |
| Carboxymethylcellulose sodium | 5 parts |
| Polyacrylic acid | 2 parts |
| Tartaric acid | 0.3 part |
| Methyl paraoxybenzoate | 0.1 part |
| Propyl paraoxybenzoate | 0.05 part |
| Dihydroxy aluminum aminoacetate | 0.3 part |
| Purified water | q.s. |
| Total amount | 100 parts |

The above components are mixed in the same manner as in Example 1 to give a base. The obtained base is applied onto and spread over a non-woven fabric at 1000 g/m² and to the base is adhered a liner made of polyethylene terephthalate processed with silicone. The obtained preparation is cut into a desired size to give an external preparation for application to the skin which has a pH value of 7 and contains 5 mg/cm² of lidocaine.

Comparative Example 1

| Lidocaine | 5 parts |
| --- | --- |
| White vaseline | 25 parts |
| Stearyl alcohol | 25 parts |
| Propylene glycol | 10 parts |
| Polyacrylic acid | 2 parts |
| Polyoxyethylated hardend castor oil | 4 parts |
| Methyl paraoxybenzoate | 0.1 part |
| Propyl paraoxybenzoate | 0.05 part |
| Purified water | q.s. |
| Total amount | 100 parts |

White vaseline and stearyl alcohol are melted on a water bath, mixed well together and kept at about 75° C.

Thereto are added a solution of lidocaine in purified water, polyacrylic acid, polyoxyethylated hardened castor oil and propylene glycol, and methyl paraoxybenzoate and propyl paraoxybenzoate and the mixture is stirred at room temperature until the mixture is solidified to give an ointment which has a pH value of 7 and contains 50 mg/g of lidocaine.

Comparative Example 2

| Lidocaine | 5 parts |
|---|---|
| Adhesive plaster base | 90 parts |
| Propylene glycol | 5 parts |
| Total amount | 100 parts |

A solution of lidocaine in propylene glycol is added to an adhesive plaster base and the base is applied onto and spread over a non-woven fabric at 1000 g/m² in accordance with a conventional method for preparing an adhesive plaster to give a plaster containing 5 mg/cm² of lidocaine.

Comparative Example 3

| Lidocaine | 10 parts |
|---|---|
| Propylene glycol | 10 parts |
| Styrene-isoprene-styrene (SIS) block copolymer | 30 parts |
| Alicyclic saturated hydrocarbon petroleum resin | 45 parts |
| Liquid paraffin | 4 parts |
| Dibutylhydroxytolune | 1 part |
| Total amount | 100 parts |

The above components other than lidocaine and propylene glycol are dissolved with heating and thereto is added a solution of lidocaine in propylene glycol and the mixture is stirred. Then, the mixture is applied onto and spread over a suitable non-woven fabric at 500 g/m² and cooled. This base is laminated with polyethylene terephthalate film and the obtained laminate is cut into a desired size to give an external preparation for application to the skin which contains 5 mg/cm² of lidocaine.

Experiment 1

Using Franz diffusion cell, there was measured an amount of lidocaine which permeated through the skin taken from the rat abdomen by HPLC. The external preparations of Examples 1 to 5 and Comparative Examples 2 and 3 were punched into a circle of 1.7 cm diameter (containing 11.35 mg or 22.7 mg of lidocaine). and the obtained circular preparations were adhered onto the rat skin in the diffusion cell. Using a phosphate buffer (pH 6.8) in a receptor, the samples were removed from the cell at a constant interval and an amount of the drug which permeated through the skin was measured. As to the ointment of Comparative Example 1, it was applied onto the rat skin within a circle of 1.7 cm diameter and the same experiment was conducted.

The results are shown in FIG. 1. As is clear from FIG. 1, the drugs permeated through the rat skin with the passage of time in case of the preparations of Examples 1 to 5 and Comparative Example 1, and hence, the permeability of the preparations of Examples 1 to 5 and Comparative Example 1 were higher than that of the preparations of Comparative Examples 2 and 3.

Experiment 2

After removing hair from the back of rats, the preparations of Examples 1 to 5 and Comparative Examples 2 and 3 which were cut into a size of 4 cm×4 cm (containing 80.0 mg or 160.0 mg of lidocaine) were adhered onto the back. While adhering the preparations, each 0.5 ml of blood was taken from rats at a constant interval and an amount of lidocaine in serum was measured by fluorescent polarization immunoassay. As to the ointment of Comparative Example 1, 1.6 g of the ointment (containing 80.0 mg of lidocaine) was applied onto a gauze of 4 cm×4 cm and the same experiment was conducted.

Figure 2:
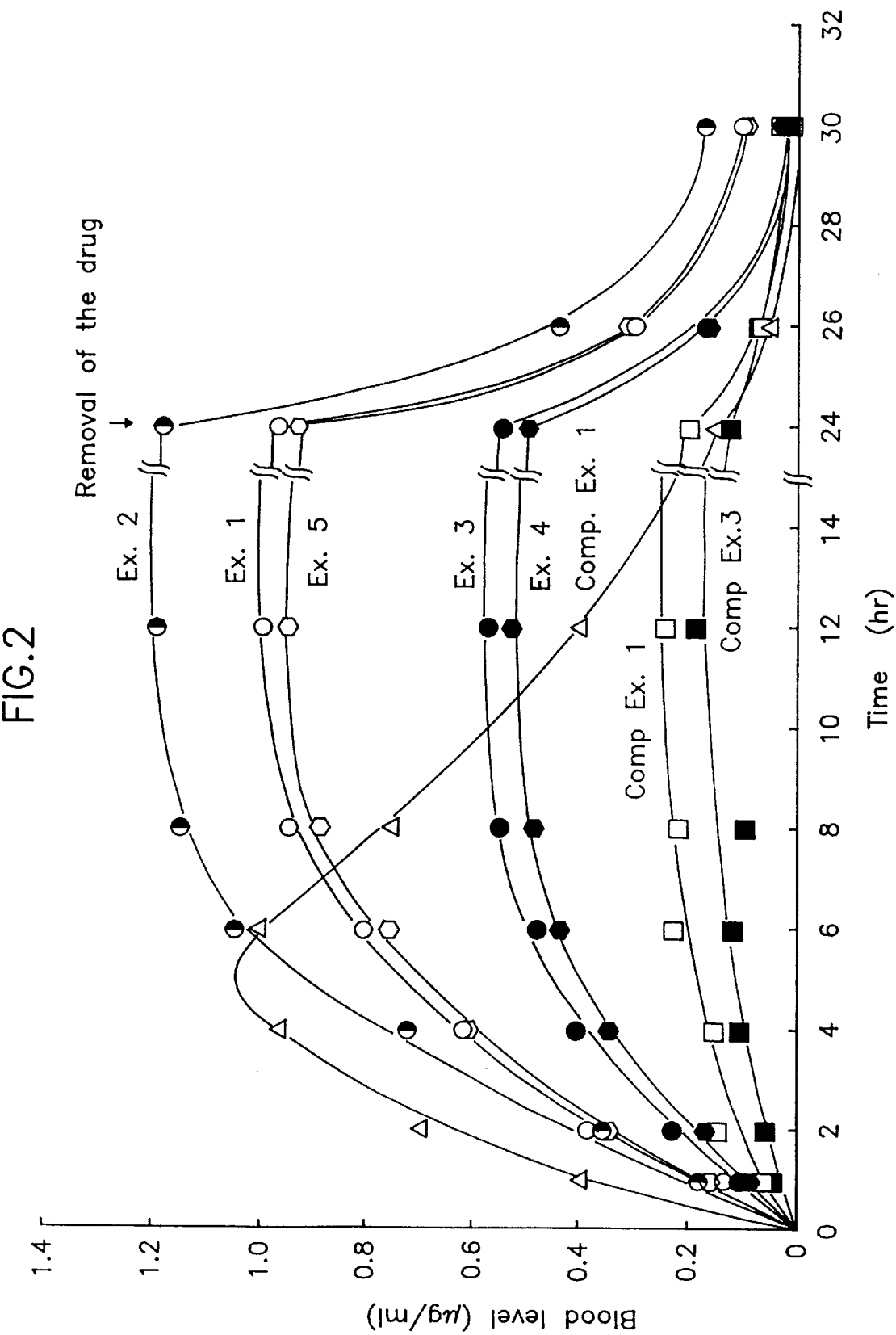
FIG. 2 is a graph showing a mean blood level with the passage of time in case of the preparations of Examples 1 to 5 in comparison with the ointment of Comparative Example 1 and the plasters of Comparative Examples 2 and 3.

The results are shown in FIG. 2 (n=4). As is clear from FIG. 2, in case of the preparations of Examples 1 to 5, blood level of lidocaine reached at a constant level six to eight hours after the administration of the drug and was maintained at that level until 24 hours after the administration, showing higher blood level than that of the preparations of Comparative Examples 1 to 3. After removing the drug, blood level was drastically lowered in case of the preparations of Examples 1 to 5. As to the ointment of Comparative Example 1, blood level was quickly increased after the administration of the drug but did not last, i.e. blood level reached at a peak four to five hours after the administration and thereafter decreased. The preparations of Comparative Examples 2 and 3 had a poor transdermal absorbability, and hence, blood level was low.

Experiment 3

After removing hair from the back of guinea pig, stimulus of a strength was given to the back with a mandolin string to confirm a normal contraction reaction of epidermis. Then, the preparations of Examples 1 to 5 and Comparative Examples 2 and 3 which were cut into a size of 4 cm×4 cm (containing 80.0 mg or 160.0 mg of lidocaine) were adhered onto the back. The preparations were removed from the back at a constant interval and stimuli were given to the adhered portion six times with the mandolin string. When the contraction reaction of the skin was not observed more than three times, a local anesthetic action of the preparation was regarded as positive. As to the ointment of Comparative Example 1, 1.6 g of the ointment (containing 80.0 mg of lidocaine) was applied onto a gauze of 4 cm×4 cm and the same experiment was conducted.

The results are shown in Table 1 (n=5). As is clear from Table 1, in case of the preparations of Examples 1 to 5, the effect was observed four hours after the administration and lasted until the preparation was removed from the back, showing a high effect rate. After removing the preparation from the back, the effect was quickly disappeared. As to the ointment of Comparative Example 1, a high effect was observed four to eight hours after the administration but did not last. The preparation of Comparative Example 2 showed but a low effect four hours after the adminstration and the preparation of Comparative Example 3 did not show any effect.

TABLE 1

| | Effect rate of local anesthesis (%) | | | | | | |
|---|---|---|---|---|---|---|---|
| | Time after adherance or application (hr) | | | | Time after removal of preparation (hr) | | |
| | 4 | 8 | 12 | 24 | 1 | 2 | 6 |
| Ex. 1 | 60 | 100 | 100 | 80 | 80 | 60 | 20 |
| Ex. 2 | 80 | 100 | 100 | 80 | 100 | 80 | 20 |
| Ex. 3 | 60 | 80 | 80 | 80 | 20 | 20 | 0 |
| Ex. 4 | 60 | 80 | 80 | 60 | 20 | 20 | 0 |

TABLE 1-continued

| | Effect rate of local anesthesis (%) | | | | | | |
|---|---|---|---|---|---|---|---|
| | Time after adherance or application (hr) | | | | Time after removal of preparation (hr) | | |
| | 4 | 8 | 12 | 24 | 1 | 2 | 6 |
| Ex. 5 | 60 | 100 | 100 | 80 | 60 | 60 | 20 |
| Comp. Ex. 1 | 80 | 80 | 60 | 20 | 0 | 0 | 0 |
| Comp. Ex. 2 | 0 | 20 | 40 | 20 | 20 | 0 | 0 |
| Comp. Ex. 3 | 0 | 0 | 0 | 0 | 0 | 0 | 0 |

What is claimed is:

1. An external preparation for application to the skin containing lidocaine which comprises a drug-retaining layer placed on a support, wherein said drug-retaining layer comprises an adhesive gel base and 1 to 10% by weight of lidocaine, said base consisting essentially of 0.5 to 50% by weight of a water-soluble high molecular weight substance selected from the group consisting of gelatin, starch, agar, mannan, alginic acid, polyacrylic acid, a salt of polyacrylic acid, dextrin, methylcellulose, methylcellulose sodium, carboxymethylcellulose, carboxymethylcellulose sodium, polyvinyl alcohol, polyvinyl pyrrolidone, copolymer of methyl vinyl ether and maleic anhydride, gum arabic, tragacanth, karaya gum and locust bean gum, 30 to 70% by weight of water and 1 to 70% by weight of a water-retaining agent selected from the group consisting of ethylene glycol, diethylene glycol, polyethylene glycol, glycerin, sorbitol, martitol, propylene glycol and 1,3-butylene glycol, said lidocaine being dissolved in the base so as to result in a uniform base material.

2. The external preparation of claim 1 wherein said adhesive gel base is capable of controlling the release of drug and has a pH value of 5 to 9.

3. The external preparation of claim 1 wherein the water content of said adhesive gel base is 20 to 50% by weight.

4. The external preparation according to claim 1, wherein said adhesive gel base consists essentially of 0.5 to 50% by weight of a water-soluble high molecular weight substance selected from the group consisting of gelatin, starch, agar, mannan, alginic acid, polyacrylic acid, a salt of polyacrylic acid, dextrin, methylcellulose, methylcellulose sodium, carboxymethylcellulose, carboxymethylcellulose sodium, polyvinyl alcohol, polyvinyl pyrrolidone, copolymer of methyl vinyl ether and maleic anhydride, gum arabic, tragacanth, karaya gum and locust bean gum, 30 to 70% by weight of water and 1 to 70% by weight of a water-retaining agent selected from the group consisting of ethylene glycol, diethylene glycol, polyethylene glycol, glycerin, sorbitol, martitol, propylene glycol and 1,3-butylene glycol; an absorbing agent and a surfactant, said lidocaine being dissolved in the base so as to result in a uniform base material.

5. The external preparation of claim 4 wherein said absorbing agent is selected from the group consisting of salicylic acid, hyaluronic acid, oleic acid, N,N-diethyl-m-toluamide, n-butyl stearate, benzyl alcohol, isopropyl myristate, isopropyl palmitate, polypropylene glycol, crotamiton, diethyl sebacate, N-methylpyrrolidone, N-ethylpyrrolidone and lauryl alcohol, and said surfactant is selected from the group consisting of polyoxyethylene sorbitan monooleate, polyoxyethylene sorbitan monostearate, sorbitan monooleate and sorbitan monopalmitate.

6. The composition according to claim 1, wherein said water is present in an amount of 34.55% to 70% by weight.

* * * * *

UNITED STATES PATENT AND TRADEMARK OFFICE
CERTIFICATE OF CORRECTION

PATENT NO.        : 5,827,529
APPLICATION NO.   : 08/258378
DATED             : October 27, 1998
INVENTOR(S)       : Masahiro Ono et al.

It is certified that error appears in the above-identified patent and that said Letters Patent is hereby corrected as shown below:

<u>Claim 3, Column 10, Line 2</u>:

The line reading "content of said adhesive gel base is 20 to 50% by weight." should read -- content of said adhesive gel base is 30 to 50% by weight. --

Signed and Sealed this

Fourth Day of August, 2009

JOHN DOLL
*Acting Director of the United States Patent and Trademark Office*